(12) United States Patent
Kim

(10) Patent No.: US 7,526,344 B2
(45) Date of Patent: Apr. 28, 2009

(54) MEDICAL DEVICE FOR TREATING PROSTATE DISEASES BY USING NEAR-INFRARED LED

(76) Inventor: Jin-Il Kim, 2282-2, Daehwa-dong, Itson-gu, Goyang-si, Gyeonggi-do (KR) 411-806

( * ) Notice: Subject to any disclaimer, the term of this patent is extended or adjusted under 35 U.S.C. 154(b) by 442 days.

(21) Appl. No.: 10/579,268

(22) PCT Filed: Nov. 10, 2004

(86) PCT No.: PCT/KR2004/002907

§ 371 (c)(1),
(2), (4) Date: May 12, 2006

(87) PCT Pub. No.: WO2005/046792

PCT Pub. Date: May 26, 2005

(65) Prior Publication Data

US 2007/0083080 A1 Apr. 12, 2007

(30) Foreign Application Priority Data

Nov. 14, 2003 (KR) .................... 10-2003-0080780

(51) Int. Cl.
*A61N 1/00* (2006.01)
(52) U.S. Cl. .................... 607/138; 607/100; 607/88
(58) Field of Classification Search ................ 600/102; 606/197; 607/86, 88, 96, 100, 138
See application file for complete search history.

(56) References Cited

U.S. PATENT DOCUMENTS

| | | | | |
|---|---|---|---|---|
| 1,381,194 A | * | 6/1921 | Homan | 606/197 |
| 2,342,557 A | * | 2/1944 | Ross et al. | 601/134 |
| 4,002,164 A | * | 1/1977 | Bradley | 601/135 |
| 4,404,881 A | * | 9/1983 | Hanifl | 83/167 |
| 4,804,240 A | * | 2/1989 | Mori | 607/88 |
| 4,911,149 A | * | 3/1990 | Borodulin et al. | 601/46 |
| 4,934,382 A | * | 6/1990 | Barone, Jr. | 128/844 |
| 5,234,004 A | * | 8/1993 | Hascoet et al. | 607/116 |
| 5,404,881 A | | 4/1995 | Cathaud et al. | 128/653.1 |
| 5,454,794 A | * | 10/1995 | Narciso et al. | 607/88 |

(Continued)

FOREIGN PATENT DOCUMENTS

JP 2000233028 A * 8/2000

(Continued)

*Primary Examiner*—Roy D Gibson
*Assistant Examiner*—Kaitlyn E Helling
(74) *Attorney, Agent, or Firm*—J.C. Patents

(57) ABSTRACT

The present invention relates to a medical device for treating prostate diseases by using near-infrared LEDs (light emitting diodes), and more particularly, to a medical device for treating prostate diseases in which a probe having installed therein near-infrared LEDs and a vibrator is constructed to be inserted into the rectum, to radiate near-infrared rays to the prostate from a position closest to the prostate and render a direct physical massage function to the prostate, thereby effectively treating prostate-related diseases. Also, the present invention relates to a pad mechanism supplementing the probe mechanism, being brought into close contact with the perineal region to radiate red visible rays and transmit vibration to the organs around the prostate, thereby curing the natures of diseases in the organs around the prostate, and a disposable probe condom used in a state in which it is worn over the probe mechanism.

5 Claims, 4 Drawing Sheets

U.S. PATENT DOCUMENTS

| | | | | |
|---|---|---|---|---|
| 5,482,053 A | * | 1/1996 | Kelly | 128/844 |
| 5,861,000 A | * | 1/1999 | Takashima | 606/197 |
| 6,187,029 B1 | * | 2/2001 | Shapiro et al. | 607/88 |
| 6,290,712 B1 | * | 9/2001 | Nordquist et al. | 607/88 |
| 6,409,744 B1 | * | 6/2002 | Marchesi | 607/96 |
| 2002/0040200 A1 | * | 4/2002 | Takashima | 601/137 |
| 2002/0187533 A1 | * | 12/2002 | Mross et al. | 435/173.1 |
| 2002/0198575 A1 | * | 12/2002 | Sullivan | 607/88 |

FOREIGN PATENT DOCUMENTS

| | | | |
|---|---|---|---|
| JP | 2004016762 A | * | 1/2004 |
| KR | 0170727 | | 11/1999 |
| KR | 1020000031549 | | 6/2000 |
| KR | 0325750 | | 8/2003 |
| KR | 0326016 | | 8/2003 |
| KR | 2005088825 A | * | 9/2005 |
| WO | WO 9524170 A1 | * | 9/1995 |
| WO | WO 0040294 A1 | * | 7/2000 |

* cited by examiner

[Fig. 1]
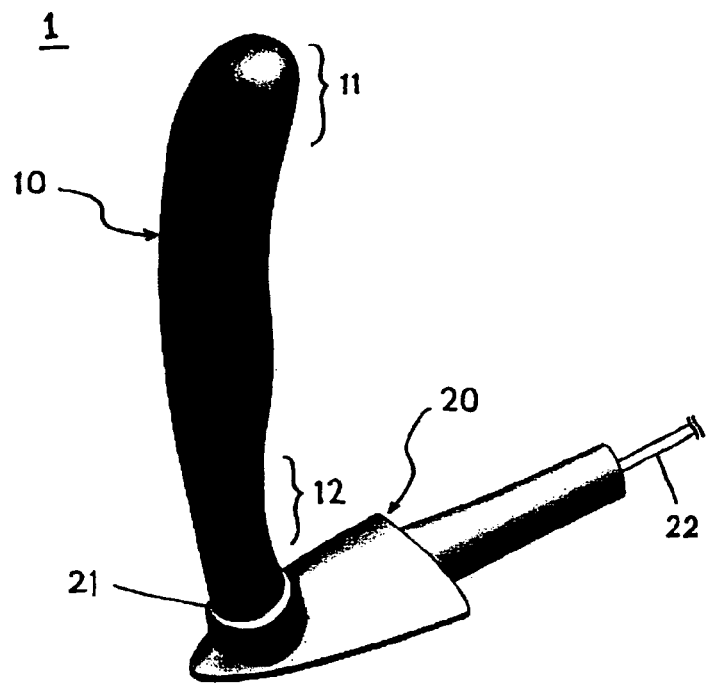
[Fig. 2]
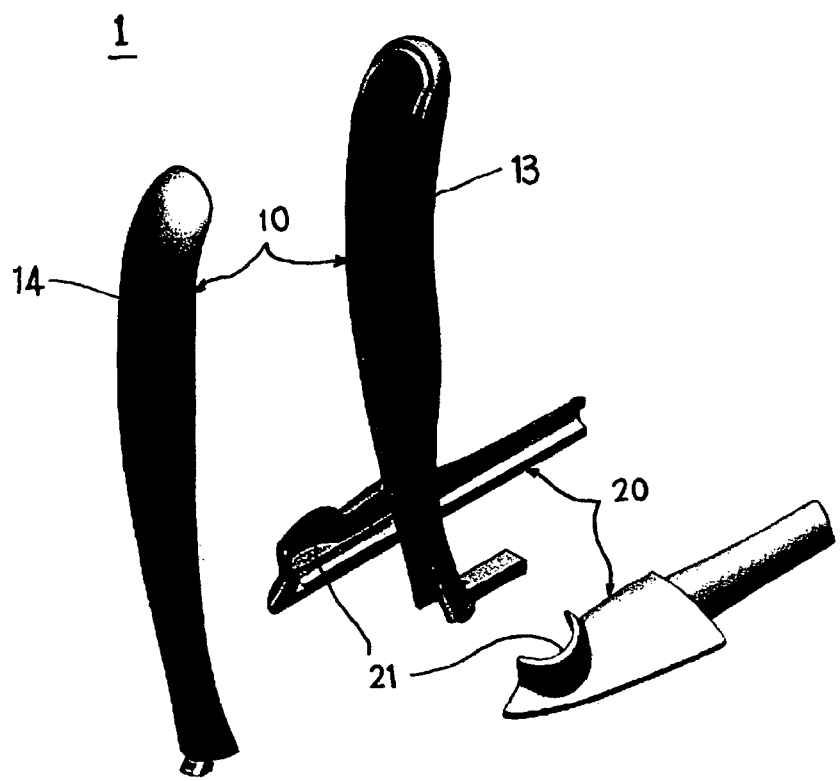

[Fig. 3]
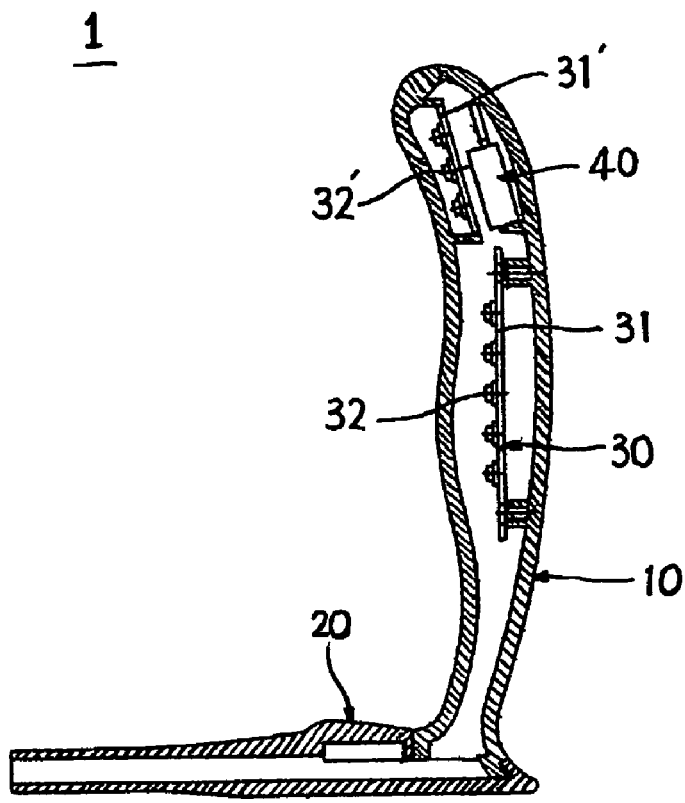
[Fig. 4]
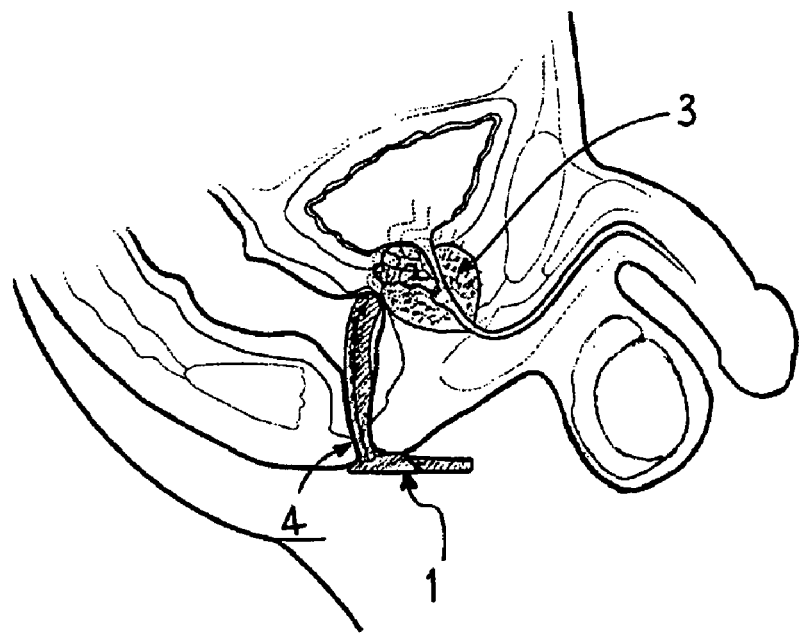

[Fig. 5]
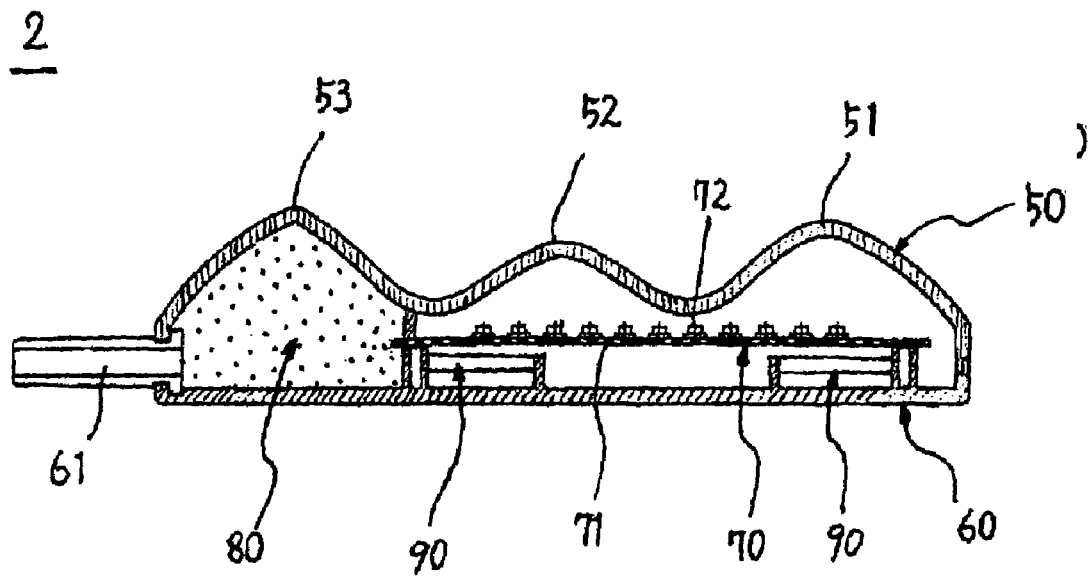
[Fig. 6]
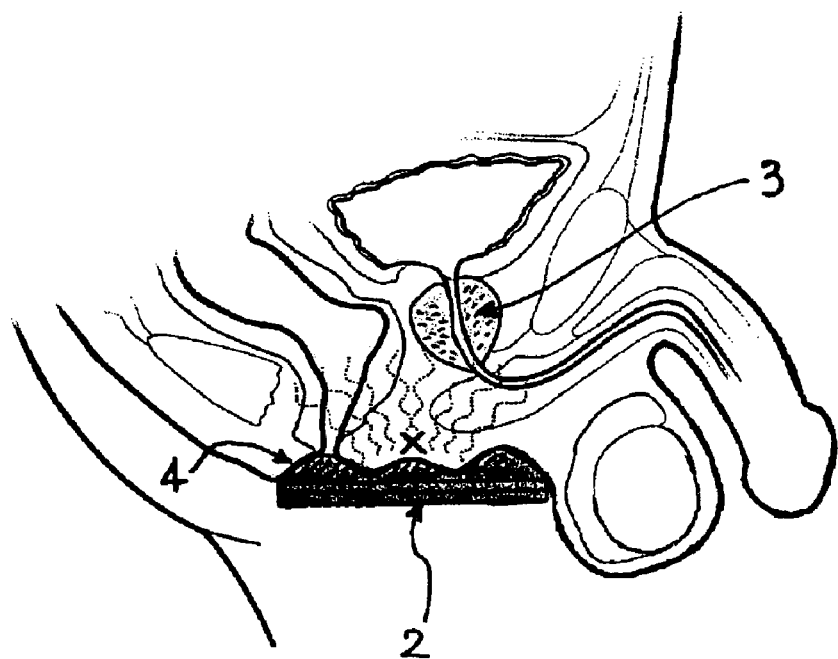

[Fig. 7]
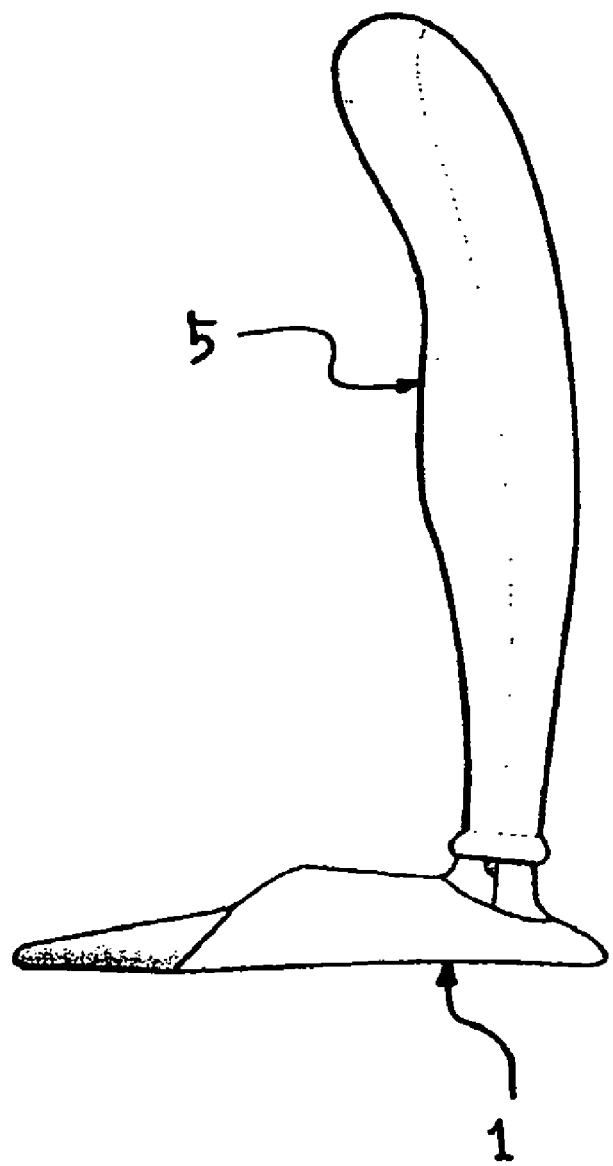

MEDICAL DEVICE FOR TREATING PROSTATE DISEASES BY USING NEAR-INFRARED LED

TECHNICAL FIELD

The present invention relates to a medical device for treating prostate diseases by using near-infrared light emitting diodes (hereinafter, referred to as "LEDs", and more particularly, to a medical device for treating prostate diseases in which a probe has installed therein near-infrared LEDs and a vibrator is constructed to be inserted into the rectum, to radiate near-infrared rays to the prostate from a position closest to the prostate and render a direct physical massage function to the prostate, thereby effectively treating prostate-related diseases.

BACKGROUND ART

Recently, prostate-related diseases have been recognized as most frequently affecting adult men, and many men suffer from prostatitis, benign prostatic hyperplasia (BPH), prostate cancer, impotence, etc. Among them, prostatitis is a disease which is most common to adult men below 50 years old. According to the statistics in U.S.A., as a result of investigating patients having urinary disorders, it was found that about 25% of the patients have a symptom of prostatitis. It was known that about 50% of men experience a symptom of prostatitis through a lifetime. Specifically, a source and a treatment method of the prostatitis have been not found yet. For this reason, prostatitis is called a 'wastebasket of clinical ignorance'. Methods for treating prostatitis known in the art so far include pharmacotherapy using an antibiotic or an alpha blocker, a standard therapy such as massage of the prostate and sitz bath, and surgical treatment such as microwave hyperthermia and laserthermia.

Benign prostatic hyperplasia occurs frequently next to prostatitis. As a man gets the age of 50, a hypertrophic lesion starts to form in the prostate. If the prostate which surrounds an outlet of the bladder is enlarged, since the urethra is narrowed due to compression of the outlet of the bladder, urine discharged from the bladder becomes slim. As a degree of enlargement of the prostate increases, urinary obstruction is caused. It was reported that benign prostatic hyperplasia prevails about 50% of 50s, about 60% of 60s and about 70% of 70s. Therefore, it is to be understood that the benign prostatic hyperplasia is regarded as a serious adult male disease which deteriorates the quality of life. As a method for treating the benign prostatic hyperplasia, a transurethral needle ablation (TUNA), a high intensity focused ultrasound (HIFU) for causing necrosis of prostate tissues using radio waves, and a transurethral resection of the prostate (TURP) as a surgical therapy are known in the art. While a pharmacotherapy is also implemented, difficulties are provoked due to peculiarity of the prostate tissues.

Prostate cancer is regarded as a devastating disease which most severely affects a patient. Prostate cancer is a malignant tumor which starts to form around the prostate. No symptom is revealed in an initial stage of development. Once a symptom is revealed, it is often the case that prostate cancer is rapidly metastasized to the bones and other major organs such as the lung, and so forth. In U.S., an incidence of the prostate cancer increases so fast as one of six males is confronted by the danger to be caught by prostate cancer. However, if diagnosis of prostate cancer is established at an early stage, a significant treatment effect can be expected such that a 10 years survival rate approaches to 80%. As a method for treating prostate cancer, pharmacotherapy, surgical therapy, radiotherapy, and hormone therapy are known in the art.

Another serious disorder resulting from prostate-related diseases as described above is impotence. Impotence which results by the occurrence of and in the course of treating chronic prostatitis, benign prostatic hyperplasia and prostate cancer, imposes an adverse influence on the quality of men's life, next to prostate cancer. As a method for treating impotence, pharmacotherapy, injection therapy, surgical therapy, etc. are known in the art.

Although various methods for treating prostate-related diseases as described above have already been known in the art, since the prostate is positioned at a complex region of the human body and the peculiarity of the prostate tissues and the source of prostate diseases are not unveiled yet, problems and harmful effects are induced. To cope with these limits and problems existing in the conventional treatment methods, a near-infrared treatment device has been developed. The near-infrared treatment device is based on a technique revealed by "project for studying plant growth in space" of the National Aeronautics and Space Administration (NASA). The NASA has been developed a light emitting diode which generates powerful light, with an aim of studying plant growth in a space. Thereafter, Wisconsin Medical College residing at Milwaukee demonstrated that a therapy using near-infrared light emitting diodes (NIR LED) increases energy in cells and thereby attains a considerable result in treating an ulcer and a brain tumor. That is to say, it was demonstrated that light emitted from the near-infrared LED has the same wavelength as that needed to remove brain tumor, activates mitochondria of cells to thereby increase activity, and functions to adjust an increase in an amount of nitric oxide (NO) in blood. This fact was confirmed by the U.S. Food and Drug Administration (FDA).

After that, with the development of the electronic technology, diverse methods for treating various diseases using near-infrared rays emitted from the light emitting diodes have been developed. Near-infrared rays (NIR) indicates light having a wavelength range of 770-1, 400 nm which is close to visible rays among infrared rays. Near-infrared rays are also called thermal rays since they have a thermal function which is more powerful than visible rays or ultraviolet rays. Due to these characteristics, if near-infrared rays penetrate into tissues of the human body, heat is generated in the corresponding portion of the human body. Near-infrared rays penetrate to a depth of 20-80 mm under the skin, and performs disinfecting and sterilizing functions in addition to the thermal function.

Also, as described above, near-infrared rays functions to promote generation of nitric oxide in blood. If an amount of nitric oxide increases locally in the human body, blood vessels are created and physiological functionality of tissues is activated to facilitate healing of a wounded part and alleviate the pain. In 1994, the FDA confirmed that near-infrared rays having a wavelength range of 890 nm increases an amount of nitric oxide in blood to facilitate blood circulation, alleviation of pain and treatment of a wounded part. Also, it was demonstrated through clinical experiments that nitric oxide promotes phagocytosis of macrophage to aid an antibacterial action of tissues and take effects on treatment of an inflammation. Further, nitric oxide activates sexual functionality and plays an important role of aiding treatment of impotence, and is used as a material for Viagra (generic name: sildenafil) which is sexual dysfunction therapeutics.

As described above, even though near-infrared rays provide excellent advantages in that they penetrate into tissues to generate powerful heat and promote production of nitric oxide to thereby activate physiological functionality, near-infrared rays are limitedly used in treating only some diseases. In this regard, means for utilizing near-infrared rays to the treatment of prostate diseases are not developed yet.

DISCLOSURE OF INVENTION

Technical Problem

Accordingly, the present invention has been made keeping in mind the above problems occurring in the prior art, and an object of the present invention is to provide a medical device for treating prostate diseases in which a probe mechanism having installed therein near-infrared LEDs and a vibrating member is constructed to be inserted into the rectum, to radiate near-infrared rays to the prostate from a position closest to the prostate and directly and physically massage the prostate.

Another object of the present invention is to provide a medical device for treating prostate diseases which comprises the probe mechanism and a pad mechanism supplementing the probe mechanism, the pad mechanism being brought into close contact with the perineal region to radiate red visible rays and transmit vibration to the organs around the prostate, thereby curing the natures of diseases in the organs around the prostate.

Still another object of the present invention is to provide a disposable probe condom which is worn over the probe mechanism when inserting the probe mechanism into the rectum to treat prostate-related diseases.

Technical Solution

In order to achieve the first object, according to one aspect of the present invention, there is provided a medical device for treating prostate diseases, comprising: a cylindrical probe housing having a massaging section which is formed at an upper part of the probe housing and inclined forward and an anus support section which is formed at a lower part of the probe housing and has a diameter smaller than that of the massaging section; a base member having one end which is defined with a hole in which a lower end of the probe housing is inserted to be supported by the base member in a longitudinal direction and the other end in which electric lines connected to a power source and a controller are installed; a light emitting member having a plate which is installed in the probe housing to extend in the longitudinal direction and a plurality of light emitting diodes which are attached to a front surface of the plate to emit near-infrared rays; and a vibrating member fixedly installed in the probe housing.

In order to achieve the second object, according to another aspect of the present invention, there is provided a medical device for treating prostate diseases, comprising: a probe mechanism used in a state in which it is inserted through an anus, and a pad mechanism used in a state in which it is brought into contact with a perineal region, the probe mechanism comprising a cylindrical probe housing having a massaging section which is formed at an upper part of the probe housing and inclined forward and an anus support section which is formed at a lower part of the probe housing and has a diameter smaller than that of the massaging section; a base member having one end which is defined with a hole in which a lower end of the probe housing is inserted to be supported by the base member in a longitudinal direction and the other end in which electric lines connected to a power source and a controller are installed; a light emitting member having a plate which is installed in the probe housing to extend in the longitudinal direction and a plurality of light emitting diodes which are attached to a front surface of the plate to emit near-infrared rays; and a vibrating member fixedly installed in the probe housing; and the pad mechanism comprising an upper plate member having an anus massaging section, a perineal region massaging section and a heat-insulating section which are sequentially formed as rounded projections; a lower plate member coupled to the upper plate member and having one end in which electric lines connected to a power source and a controller are installed; a light emitting member having a plate which is installed on the lower plate member to be positioned below the anus massaging section and the perineal region massaging section of the upper plate member and a plurality of light emitting diodes which are attached to an upper surface of the plate to emit red visible rays; heat-insulating filler filled in a space defined between the heat-insulating section of the upper plate member and the lower plate member; and a vibrator fixedly installed between the upper and lower plate members.

In order to achieve the third object, according to still another aspect of the present invention, there is provided a probe condom for a medical device for treating prostate diseases, wherein the probe condom is worn as a disposable over a probe mechanism for rendering a hyperthermia or performing a massaging function when inserting the probe mechanism into the rectum to treat prostate-related diseases, the probe condom being made of resilient latex material and applied on a surface thereof with a lubricant.

BRIEF DESCRIPTION OF THE DRAWINGS

Further objects and advantages of the invention can be more fully understood from the following detailed description when taken in conjunction with the accompanying drawings in which:

FIG. 1 is a perspective view illustrating a probe mechanism according to the present invention;

FIG. 2 is an exploded perspective view illustrating a probe housing and a support element of the probe mechanism shown in FIG. 1;

FIG. 3 is a longitudinal cross-sectional view illustrating the probe mechanism according to the present invention;

FIG. 4 is a conceptual view illustrating an in-use state of the probe mechanism according to the present invention;

FIG. 5 is a longitudinal cross-sectional view illustrating a pad mechanism according to the present invention;

FIG. 6 is a conceptual view illustrating an in-use state of the pad mechanism according to the present invention; and FIG. 7 is a conceptual view illustrating an in-use state of a probe condom according to the present invention.

BEST MODE FOR CARRYING OUT THE INVENTION

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a perspective view illustrating a probe mechanism according to the present invention; FIG. 2 is an exploded perspective view illustrating a probe housing and a support element of the probe mechanism shown in FIG. 1; FIG. 3 is a longitudinal cross-sectional view illustrating the probe mechanism according to the present invention; and FIG. 4 is a conceptual view illustrating an in-use state of the probe mechanism according to the present invention.

A medical device for treating prostate diseases in accordance with an embodiment of the present invention includes a probe mechanism 1. The probe mechanism 1 is used in a state in which it is inserted into the rectum through the anus 4. The probe mechanism 1 comprises a probe housing 10, a base member 20, a light emitting member 30, and a vibrating member 40. When viewed in its entirety, the probe housing 10 has a cylindrical configuration which has a wide upper end and a narrow lower end. A massaging section 11 is formed at an upper part of the probe housing 10 and is slightly curved. An anus support section 12 is formed at a lower part of the probe housing 10 and has a diameter smaller than that of the massaging section 11.

When the probe housing 10 is inserted into the rectum, the massaging section 11 approaches closest the prostate 3 so that the prostate 3 is positioned at a distance of no greater than about 60 mm from the massaging section 11, and a narrow portion of the anus support section 12 is positioned at the sphincter of the anus 4 so that the anus support section 12 is stably held.

In the preferred embodiment of the present invention, the probe housing 10 comprises a front plate element 13 and a rear plate element 14 which are coupled to each other in the longitudinal direction. The front plate element 13 is made of transparent or semi-transparent synthetic resin so that near-infrared rays can easily penetrate the front plate element 13. The rear plate element 14 is made of opaque synthetic resin. Nano-sized silver powders having a grain size of 5-10 nm may be deposited to the front plate element 13 and the rear plate element 14.

The probe housing 10 is erected on the base member 20 to extend in a longitudinal direction. A hole 21 is defined at one end of the base member 20 so that a lower end of the probe housing 10 can be inserted into the hole 21 to be supported by the base member 20. Electric lines 22 connected to a power source and a controller (not shown) are laid in the other end of the base member 20.

The light emitting member 30 and the vibrating member 40 are disposed in the probe housing 10. The light emitting member 30 comprises a plate 31 and a plurality of light emitting diodes 32 installed on the plate 31. The light emitting diodes 32 are installed on a front surface of the plate 31 to face the front plate element 13. At least 90% of the light emitting diodes 32 of the light emitting member 30 emit near-infrared rays having a wavelength range of 830-930 nm. However, since the near-infrared rays having this wavelength range is not viewed with naked eyes, in the present invention, the remaining at most 10% of the light emitting diodes 32 may emit visible rays to allow a user to confirm an operating state of the probe mechanism 1. For example, red light emitting diodes having a wavelength range of 600-700 nm may be used. While the plate 31 and the light emitting diodes 32 may have a single structure, as occasion demands, a plate 31' and a plurality of light emitting diodes 32' may be separately provided to the massaging section 11 to form another structure.

Further, although any vibrators may be used as the vibrating member 40 so long as they can be installed in the probe housing 10, it is preferable to use an electronic vibrator having a speed of 10,000 rpm among electronic vibrators which are commercially available. The electronic vibrator is fixedly installed on an inner surface of the rear plate element 14 at the massaging section 11.

In the present invention, a number of rubbing protrusions (not shown) may be formed on a surface of the massaging section 11 of the probe housing 10. Also, it can be envisaged that an articulated joint (not shown) is installed between the plates 31 and 31' to allow an inclination angle of the massaging section 11 to be adjusted.

A medical device for treating prostate diseases in accordance with another embodiment of the present invention includes a probe mechanism 1 and a pad mechanism 2 supplementing the probe mechanism 1. The probe mechanism 1 is constructed in the same manner as described above. The pad mechanism 2 is constructed as shown in FIG. 5. FIG. 6 is a conceptual view illustrating an in-use state of the pad mechanism 2.

Referring to FIGS. 5 and 6, the pad mechanism 2 is used in a state in which it is brought into contact with the perineal region and the anus 4. The pad mechanism 2 comprises an upper plate member 50, a lower plate member 60, a light emitting member 70, a heat-insulating filler 80, and vibrating members 90.

The upper plate member 50 serves as a cover for covering the pad mechanism 2. The upper plate member 50 has an anus massaging section 51, a perineal region massaging section 52 and a heat-insulating section 53 which are sequentially formed as rounded projections. The lower plate member 60 is coupled to the upper plate member 50 with a space defined therebetween. The lower plate member 60 has one end in which electric lines 61 connected to a power source and a controller (not shown) are laid. In the present invention, it is preferred that the upper plate member 50 be made of transparent or semi-transparent synthetic resin so that near-infrared rays can easily penetrate the upper plate member 50. As occasion demands, vent holes (not shown) may be defined entirely or partly in the upper plate member 50, and rubbing protrusions (not shown) may be formed on a surface of the upper plate member 50.

The light emitting member 70, the heat-insulating filler 80 and the vibrating members 90 are disposed in the space defined between the upper plate member 50 and the lower plate member 60. The light emitting member 70 has a plate 71 which is installed on the lower plate member 60 and a plurality of light emitting diodes 72 which are attached to the plate 71 in such a way as to face the upper plate member 50. The light emitting member 70 is installed to be positioned only below the anus massaging section 51 and the perineal region massaging section 52 of the upper plate member 50. In the present invention, in consideration of a purpose of use and an economy, light emitting members 30 and 70 having different wavelength ranges are employed to constitute the probe mechanism 1 and the pad mechanism 2, respectively. That is to say, at least 90% of the light emitting diodes 32 installed in the probe mechanism 1 emit near-infrared rays having a wavelength range of 830-930 nm, and at least 90% of the light emitting diodes 72 installed in the pad mechanism 2 emit red visible rays having a wavelength range of 600-700 nm. The remaining at most 10% of the light emitting diodes 32 and 72 of the probe and pad mechanisms 1 and 2 emit near-infrared rays and/or red visible rays.

The heat-insulating filler 80 such as silicon is filled between the heat-insulating section 53 of the upper plate member 50 and the lower plate member 60. The heat-insulating filler 80 functions to prevent heat and light generated by the light emitting member 70 from affecting other organs, particularly, testicles. As well known in the art, if a temperature of the testicles rises, it adversely influences the production of spermatozoon. The vibrating member 90 may comprise the same electronic vibrator as that constituting the vibrating member 40 of the probe mechanism 1. It is preferred that the vibrating members 90 be installed on the lower plate member 60 not to block the rays emitted from the light emitting diodes 72.

The pad mechanism 2 according to the present invention serves to supplement the probe mechanism 1. By positioning the anus massaging section 51 on the anus 4 and the heat-insulating section 53 adjacent to the testicles, the perineal region massaging section 52 is brought into close contact with the perineal region. The pad mechanism 2 provides a hyperthermic effect and a massaging effect to the organs positioned around the prostate 3, for example, the perineal region, the anus 4 and the urethra, to alleviate various symptoms arising in the organs due to prostate diseases. As a result, the pad mechanism 2 performs a supplementing function by aiding the treatment of prostate diseases.

In the meanwhile, when inserting the probe mechanism 1 constituting the medical device for treating prostrate diseases according to the present invention into the rectum, it is effective that the probe mechanism 1 is used in a state in which it is worn by a probe condom 5 made of resilient latex material. FIG. 7 is a conceptual view illustrating an in-use state of the probe condom 5 in accordance with still another embodiment of the present invention. As a matter of fact, it is not easy or pleasant to insert the probe mechanism 1 through the anus 4. Moreover, after the probe mechanism 1 is used, the probe mechanism 1 must be kept in a place in a cleanly washed state. If the probe housing 1 is contaminated with bacteria or foreign substances while being kept in the place, the bacteria or foreign substances may transfer to the rectum to develop a disease. To cope with this problem and ensure easy manipulation of the probe mechanism 1, it is preferable to employ the disposable probe condom 5.

The probe condom 5 according to the present invention may be made of latex which is used as a material of the conventional condom, and a lubricant is usually applied to a surface of the probe condom 5. In this regard, in consideration of the fact that the probe condom 5 of the present invention is used for treating prostate diseases, it is preferable that the lubricant comprise medicinal liquid which is efficacious against prostate diseases, such as aloe extract. Also, in order to prevent the probe condom 5 from being released from the probe mechanism 1 while being used, a release preventing groove or a release preventing projection (not shown) may be defined or formed on an outer surface of the probe housing 10 at a lower end of the anus support section 12 so that a proximal end of the probe condom 5 can be engaged into or with the release preventing groove or the release preventing projection.

In the medical device for treating prostate diseases according to the present invention, only the probe mechanism 1 may be used or the probe mechanism 1 and the pad mechanism 2 may be commonly used, depending upon a patient's condition or when occasion demands. Preferably, by using the probe mechanism 1 with the probe condom 5 worn over the probe mechanism 1, a treatment procedure can be implemented in a convenient manner, and a treatment effect can be improved.

The probe mechanism 1 and the pad mechanism 2 are connected to the power sources and controllers (not shown) by way of the electric lines 22 and 61. The power sources may supply direct current or alternate current, and it is more convenient to use rechargeable batteries. The controllers function to control operations of the light emitting members 30 and 70 and the vibrating members 40 and 90.

The probe mechanism 1 and the pad mechanism 2 according to the present invention may be used in a state in which they are connected with other medical appliances related with the prostate 3, for example, for photographing a shape and a size of the prostate 3, or with diagnosis equipment for inspecting whether or not a tuber exists on a surface of the prostate 3. A person having ordinary skill in the art will readily recognize that these usage patterns also fall within the scope of the present invention.

Since the medical device according to the present invention treats the prostate diseases such that cells of the prostate tissues are activated and regenerated, the medical device of the present invention is essentially different from the conventional implements which treat prostate diseases by burning the prostate tissues or causing necrosis of the prostate tissues through using heat generated by microwaves, ultrasonic waves, high-frequency waves, etc. Specifically, in the present invention, when transmitting energy in the form of electronic waves to the prostate, because a separate medium for transmitting energy to the prostate is not needed, heat loss is not caused while transmitting energy. Therefore, in the present invention, near-infrared rays are sufficiently transmitted through a distance of about 60 mm which is measured from the rectum to the prostate, and a temperature of 43° C. at which tumor cells die is quickly attained. As a consequence, it is possible to prevent a tumor from developing in the prostate and improve blood circulation to thereby render an optimal hyperthermia.

Also, in the present invention, due to the fact that the vibrator mounted to the probe mechanism finely massages the prostate at a speed of 10,000 rpm, pus gathered in the prostate of a patient suffering from chronic prostatitis or debris of dead cells can be discharged by a physical force, and the tissues of the prostate can be softly relaxed. In particular, penetration of medicines into the prostate tissues is facilitated by the thermal energy of the near-infrared rays and the massaging function rendered by the vibrator, whereby treating effect can be maximized.

INDUSTRIAL APPLICABILITY

As apparent from the above descriptions, the medical device for treating prostate diseases according to the present invention provides advantages in that, since near-infrared rays having various treatment functions through thermal action, an increase in an amount of nitric oxide, facilitation of blood circulation, and activation of cell movement are radiated to the prostate and its surrounding organs from the closest position, and a physical massaging function is rendered to the prostate and the perineal region, diseases of the prostate and its surrounding organs can be effectively treated.

Accordingly, by the present invention, it is possible to effectively treat patients who suffer from chronic prostate diseases and depend on an operation due to difficulties in treatment through pharmacotherapy, without conducting a surgical operation. Also, the medical device for treating prostate diseases can be conveniently manipulated, so that even an ordinary person having no expert knowledge can easily use the medical device. Further, because the medical device can be manufactured at a moderate cost due to its simple construction, the medical device according to the present invention can remarkably contribute to treatment of prostate-related diseases which debase modern people's quality of living.

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. A medical device for treating prostate diseases, comprising:

a cylindrical probe housing having a massaging section which is formed at an upper part of the probe housing and inclined forward, and an anus support section which is formed at a lower part of the probe housing and has a diameter smaller than that of the massaging section;

a base member having one end which is defined with a hole in which a lower end of the probe housing is inserted to be supported by the base member in a longitudinal direction and the other end in which electric lines connected to a power source and a controller are installed;

a light emitting member having a plate which is installed in the probe housing to extend in the longitudinal direction and a plurality of light emitting diodes which are attached to a front surface of the plate to emit near-infrared rays; and a vibrating member fixedly installed in the probe housing.

2. The medical device as set forth in claim 1, wherein the probe housing comprises a front plate element and a rear plate element which are coupled to each other in the longitudinal direction, the front plate element being made of transparent or semi-transparent synthetic resin and the rear plate element being made of opaque synthetic resin.

3. The medical device as set forth in claim 1, wherein at least 90% of the light emitting diodes of the light emitting member emit near-infrared rays having a wavelength range of 830-930 nm, and the remaining at most 10% of the light emitting diodes emit red visible rays.

4. A medical device for treating prostate diseases, comprising:

a probe mechanism used in a state in which it is inserted through an anus, and a pad mechanism used in a state in which it is brought into contact with a perineal region, the probe mechanism comprising a cylindrical probe housing having a massaging section which is formed at an upper part of the probe housing and inclined forward and an anus support section which is formed at a lower part of the probe housing and has a diameter smaller than that of the massaging section;

a base member having one end which is defined with a hole in which a lower end of the probe housing is inserted to be supported by the base member in a longitudinal direction and the other end in which electric lines connected to a power source and a controller are installed;

a light emitting member having a plate which is installed in the probe housing to extend in the longitudinal direction and a plurality of light emitting diodes which are attached to a front surface of the plate to emit near-infrared rays; and a vibrating member fixedly installed in the probe housing;

and the pad mechanism comprising an upper plate member having an anus massaging section, a perineal region massaging section and a heat-insulating section which are sequentially formed as rounded projections; a lower plate member coupled to the upper plate member and having one end in which electric lines connected to a power source and a controller are installed; a light emitting member having a plate which is installed on the lower plate member to be positioned below the anus massaging section and the perineal region massaging section of the upper plate member and a plurality of light emitting diodes which are attached to an upper surface of the plate to emit red visible rays; heat-insulating filler filled in a space defined between the heat-insulating section of the upper plate member and the lower plate member; and a vibrator fixedly installed between the upper and lower plate members.

5. The medical device as set forth in claim 4, wherein at least 90% of the light emitting diodes of the probe mechanism emit near-infrared rays having a wavelength range of 830-930 nm, at least 90% of the light emitting diodes of the pad mechanism emit red visible rays having a wavelength range of 600-700 nm, and the remaining at most 10% of the light emitting diodes of the probe and pad mechanisms emit near-infrared rays and/or red visible rays.

* * * * *